US007169398B2

(12) United States Patent
Bigbie et al.

(10) Patent No.: US 7,169,398 B2
(45) Date of Patent: Jan. 30, 2007

(54) EQUINE PROTOZOAL MYELOENCEPHALITIS VACCINE

(75) Inventors: Rocky Barry Bigbie, Spring Hill, KS (US); Terry Kaleung Ng, Fort Dodge, IA (US); Joseph Wilson Whalen, Jr., Fort Dodge, IA (US)

(73) Assignee: Wyeth, Madison, NJ (US)

( * ) Notice: Subject to any disclaimer, the term of this patent is extended or adjusted under 35 U.S.C. 154(b) by 371 days.

(21) Appl. No.: 09/840,485

(22) Filed: Apr. 23, 2001

(65) Prior Publication Data

US 2002/0041886 A1    Apr. 11, 2002

Related U.S. Application Data

(60) Provisional application No. 60/278,695, filed on Mar. 26, 2001, provisional application No. 60/199,435, filed on Apr. 25, 2000.

(51) Int. Cl.
*A61K 39/002*   (2006.01)
*A61K 39/005*   (2006.01)
*A61K 39/008*   (2006.01)

(52) U.S. Cl. .................................. 424/269.1; 435/947
(58) Field of Classification Search ............. 424/269.1, 424/234.1; 435/6, 7.22, 258.1, 7.2, 34, 7.1, 435/183; 530/350; 436/518, 528, 543
See application file for complete search history.

(56) References Cited

U.S. PATENT DOCUMENTS

| | | | | |
|---|---|---|---|---|
| 5,554,371 A | * | 9/1996 | Caputa et al. | 424/234.1 |
| 6,071,737 A | * | 6/2000 | Marsh et al. | 435/258.1 |
| 6,110,665 A | * | 8/2000 | Fenger et al. | 435/6 |
| 6,153,394 A | * | 11/2000 | Mansfield et al. | 45/7.22 |
| 6,344,337 B1 | * | 2/2002 | Mansfield et al. | 435/7.2 |
| 6,489,148 B1 | * | 12/2002 | Mansfield et al. | 435/183 |

FOREIGN PATENT DOCUMENTS

| | | | |
|---|---|---|---|
| GB | 2310135 | * | 6/1997 |
| GB | 2310212 | * | 8/1997 |
| WO | 97/29120 | * | 8/1997 |
| WO | WO 97/29770 | * | 8/1997 |
| WO | WO 99/47927 | * | 11/1999 |
| WO | WO 00/17640 | | 3/2000 |
| WO | WO 00/49049 | | 8/2000 |
| WO | WO 01/15708 A1 | | 3/2001 |
| WO | WO 01/15708 | * | 8/2001 |

OTHER PUBLICATIONS

Granstrom, D.E. et al."Equine Protozoal Myloencephalitis" Journal Veterinary Diagnostic Investigation vol. 5, pp. 88-90, 1993.*
Mrash,A.E. et al. "Description of a New Neospora Species" Journal of Parasitology, vol. 84, No. 5, pp. 983-991, 1998.*
Granstrom, D.E. et al."Equine Protozoal Myloencephalitis" Journal Veterinary Diagnostic Investigation vol. 5, pp. 88-90, 1993.*
Boslego, JW et al (1991), Chapter 17, p. 211-223, in Vaccines and immunotherapy.*
Ellis, Ronald W., Ph.D., Chapter 29, pp. 568-575, New Technologies for making vaccines, in Vaccines, 1988, WB Saunders Company, Plotin and Mortimer.*
Granstrom, DE et al, J. Vet. Diagn. Invest., vol. 5, pp. 88-90, 1993, Equine protozoal myeloencephalitis: antigen analysis of cultured *Sarcocystis neurona* merozoites.*
Dubey, JP et al, J. Eukaryot. Microbiol. 1999, Sep.-Oct. vol. 46(5), pp. 500-506, Characterization of a *Sarcocystis neurona* isolate (SN6) from a naturally infected horse from Oregon.*
Dubey, JP et al, JAVMA, vol. 215, No. 7, pp. 970-972, Oct. 1, 1999, Serologic pervalence of *Sarcocystis neurona, Toxoplasma gondii* and *Neospora caninum* in horses in Brazil.*
Dubey, JP et al, Vet. Parasitol. 1999, Sep. 15, vol. 86(1), pp. 59-62, Prevalence of antibodies to *Sarcocystis neurona, Toxoplasma gondii* and *Neospora caninum* in horses from Argentina.*
Murphy, AJ et al, J. Parasitol. Oct. 1999; vp;/ 85(5), pp. 979-981, Simplified technique for isolation, excystation and culture of *Sarcocystis* species from opossums.*
Liang, FT et al, Infection and Immunity, vol. 66(5), pp. 1834-1838, May 1998, Evidence that surface proteins Sn14 and Sn16 of *Sarcocystis neurona* merozoites are involved in Infection and Immunity.*
Liang, Fang Ting et al, Analytical Biochemistry, vol. 250, pp. 61-65, 1997, Micropreparative high resolution purification of proteins by combination of *Sodium dodecyl* sulfate polyacrylamide gel electrophoresis, isoelectric focusing and membrane blotting.*
Rossano, MG et al, J. Vet. Diagn. Invest. vol. 12, pp. 28-32, 2000, Improvement of western blot test specificity for detecting equine serum antibodies to *Sarcocystis neurona*.*
Sep. 2002, Wyeth 2002 Medical Device Company, abstract, from Pharaecutical Companies analysis, title "Structure and activities".*
US conditional approval for Fort Dodge equine vaccine, Animal-Pharm, vol. 464, p. 18, Mar. 9, 2001 (abstract only).*
Gradoni, L et al, Vaccine, vol. 23, 2005, pp. 5245-5251.*
Hagan, Paul et al, Expert. Opinion Biol. Ther. 2003, vol. 3(8), pp. 1271-1278.*
Andrianarivo, AG et al, International Journal of Parasitology, vol. 30, 2000, pp. 985-990.*
Pye, D et al, Infection and Immunity, vol. 59(7), pp. 2403-2411, Jul. 1991.*

(Continued)

*Primary Examiner*—Mark Navarro
*Assistant Examiner*—Ginny Allen Portner
(74) *Attorney, Agent, or Firm*—Adley F. Mandel; Anne M. Rosenblum

(57) ABSTRACT

The present invention provides an immunogenically active component comprising inactivated *Sarcocystis neurona* cells and/or inactivated *Neospora hughesi* cells; antigens derived therefrom; DNA derived therefrom; or a mixture; or in combination with other vaccine components; thereof. Further provided are vaccine compositions useful for preventing or ameliorating equine protozoal myeloencephalitis infection and disease and a method for the cell culture propagation of protozoan parasites.

16 Claims, No Drawings

OTHER PUBLICATIONS

Cheadle et al., Int'l Journal for Parasitology 31 (2001) 330-335, The nine-banded armadillo (*Dasypus novemcinctus*) is an intermediate host for *Sarcocystis neurona*.

Paola Minoprio, Int'l Journal for Parasitology 31 (2001) 588-591, Parasite polyclonal activators: new targets for vaccination approaches?.

Saville et al., Verterinary Parasitology 95 (2001) 211-222, Utilization of stress in the development of an equine model for equine protozoal myelocephalitis.

Lindsay, et al., Veterinary Parasitology 95 (2001) 179-186, Direct agglutination test for the detection of antibodies to *Sarcocystis neurona* in experimentally infected animals.

Cheadle et al., Veterinary Parasitology 95 (2001) 305-311, Sporocyst size of isolates of Sarcocystis shed by the Virginia opossum (*Didelphis virginiana*).

J. P. Dubey, Veterinary Parasitology 95 (2001) 341-351, Migration and development of *Sarcocystis neurona* in tissues of interferon gamma knockout mice fed sporocysts from a naturally infected opossum.

Porter, et al., Veterinary Parasitology 95 (2001) 313-319, Evaluation of the shedding of *Sarcocystis falcatula* sporocysts in experimentally infected Virginia opossums (*Didelphis virginiana*).

Dubey et al., Veterinary Parasitology 95 (2001) 283-293, Prevalence of *Sarcocystis neurona* sporocysts in opossums (*Didelphis virginiana*) from rural Mississippi.

Mansfield et al., Veterinary Parasitology 95 (2001) 167-178, Comparison of *Sarcocystis neurona* isolates derived from horse neural tissue.

Cook, et al., Veterinary Parasitology 95 (2001) 187-195, Interpretation of the detection of *Sarcocystis neurona* antibodies in the serum of young horses.

Vardeleon et al., Veterinary Parasitology 95 (2001) 273-282, Prevalence of Neospora hughesi and *Sarcocystis neurona* antibodies in horses from various geographical locations.

Cutler et al., Veterinary Parasitology 95 (2001) 197-210, Immunoconversion against *Sarcocystis neurona* in normal and dexamethasone-treated horses challenged with *S. neurona* sporocysts.

Cutler, et al., J. Parasitology 85(2) 1999 301-305, Are *Sarcocystis neurona* and *Sarcocystis falcatula* synonymous? A horse infection challenge.

Rossano et al., J Vet Diagn Invest 12:28—32 (2000), Improvement of western blot test specificity for detecting equine serum antibodies to *Sarcocystis neurona*.

Gauthier et al., J Vet Diagn Invest 11:259-265 (1999), Western immunoblot analysis for distinguishing vaccination and infection status with *Borrelia burgdorferi* (Lyme disease) in dogs.

Lindsay, et al., J Parasitology 86(1) 2000 164-166, Determination fo the Activity of Diclazuril Against *Sarcocystis neurona* and *Sarcocystis falcatula* in Cell Cultures.

Dubey et al., J Parasitology 86(1) 2000 160-163, Isolation of *Sarcocystis speeri* Dubey and Lindsay, 1999 Parasite from the south American Opossum (*Didelphis albiventris*) from Argentina.

Reed et al., AAEP Proceedings vol. 42 1996 75-78, Equine Protozoal Encephalomyelitis.

Dubey et al., J Parasitology 86(6) 2000 1276-1280, Completion of the Life Cycle of *Sarcocystis neurona*.

Dubey et al., J Parasitology 86(5) 2000 1150-1152, Immunohistochemical Confirmation of *Sarcocystis neurona* Infections in raccoons, Mink, Cat, Skunk, and Pony.

Dame et al., Parasitol Res 2000 86: 940-943, Equine protozoal myeloencephalitis: msytery wrapped in enigma.

Saville et al., JAVMA vol. 217 No. 8, 2000,1174-1185, Analysis of risk factors for the development of equine protozoal myeloencephalitis in horses.

Dubey et al., J Parasitology 84(16), 1998 1158-1164, Isolation of a Third species of Sarcocystis in Imunodeficient mice fed Feces from Opossums (*Didelphis virginiana*) and its Differentiation from *Sarcocystis falcatula* and *Sarcocystis neurona*.

Cutler et al., J Parasitology 85(2) 1999 301-305, Are *Sarcocystis neurona* and *Sarcocystis falcatlula* Synonymous? A horse Infection Challenge.

Dubey et al., J Eukaryot. Microbiol. 46(5) 1999 500-506, Characterization of a *Sarcocystis neurona* Isolate (SN6) from a Naturally Infected Horse from Oregon.

Fenger et al., Veterinary Parasitology 68 (1997) 199-213, Experimental induction of equine protozoal myeloencephalitis in horses using *Sarcocystis* sp. Sporocysts from the opossum (*Didelphia virginiana*).

Clara K. Fenger, Parasitology vol. 19, No. 4, Apr. 1997, 513-523, Equine Protozoal Myeloencephalitis.

Kisthardt et al., Equine Practice, vol. 19, No. 2, Feb. 1997, 8-13, Equine Protozoal Myeloencephalitis.

Divers et al., Supplement to Veterinary Medicine Feb. 2000, 3-22, Equine protozoal myeloencephalitis: Recent advances in diagnosis and treatment.

Saville et al., AAEP Proceedings, vol. 41, 1995 220-221, Prevalence of Serum antibodies to *Sarcocystis neurona* in Horses in Ohio, 220-221.

Saville et al., JAVMA, vol. 210, No. 4, Feb. 1997 519-524, Seroprevalence of antibodies to *Sarcocystis neurona* in horses residing in Ohio.

Fenger et al., J Parasitology 8(16) 1995 916-919, Identification of Opossums (*Didelphis virigniana*) as the Putative Definition Host of *Sarcocystis neurona*.

Reed et al., AAEP Proceedings vol. 42 1996 75-79, Equine Protozoal Encephalomyelitis.

Tanhauser et al., J Parasitology 85(2) 1999 221-228, Multiple DNA Markers Differentiate *Sarcocystis neurona* and *Sarcocystis falcatula*.

Dubey et al., Int'l J Parasitology 28 1998 1823-1828, Isolation in immunodeficient mice of *Sarcocystis neurona* from opossum (*Didelphis virginiana*) faeces, and its differentiation from *Sarcocystis falcatula*.

Marsh et al., J Parasitology 83(6) 1997 1189-1192, In Vitro Cultivation and Experimental Inoculation of *Sarcocystis falcatula* and *Sarcocystis neurona* Merozoites into Budgerigars (*Melopsittacus undulatus*).

Liang et al., Infection and Immunity vol. 66 No. 5 may 1998 1834-1838, Evidence that Surface Proteins Sn14 and Sn16 of *Sarcocystis neurona* Merozoites are Involved in Infection and Immunity.

Wilson et al., Parasitology Today vol. 14 No. 9 1998 348-353, Iron Acquisition by Parasitic Protozoa.

Granstrom et al., J Parasitology 78(5) 1992 909-912, Equine Protozoal Myelitis in Panamanian Horses and Isolation of *Sarcocystis neurona*.

Marsh et al., J Parasitology vol. 85 No. 4 Aug. 1999 750-757, Comparison of the Internal Transcribed Spacer, ITS-1, from *Sarcocystis falcatula* Isolates and *Sarcocystis neurona*.

Gajadhar et al., J Parasitology 84(4) 1998 759-763, Prevalence of Toxoplasma Gondii in Canadian Market-Age Pigs.

Fischer et al., J Parasitology 84(1) 1998 50-54, Characterization of Bovine Sarcocystis Species by Analysis of their 18S Ribosomal DNA Sequences.

Fenger et al., JAVMA vol. 210 No. 7 Apr. 1, 1997 923-927, Epizootic of Equine protozoal myeloencephalitis on a farm.

I. G. Mayhew, Cornell Vet 65 500-511 (1975), Collection of Cerebrospinal fluid from the Horse.

Speer et al., J Parasitology 86(1) 2000 25-32, Comparative Development and Merozoite Production of Two Isolates of *Sarcocystis neurona* and *Sarcocystis falcatula* in Cultured Cells.

Davis et al., J Parasitology 77(5) 1991 789-792, In Vitro Cultivation of *Sacocystis neurona* from the Spinal cord of a Horse with Equine Protozoal Myelitis.

Dubey et al., J Parasitology 86(1) 2000 160-163, Isolation of *Sarcocystis speeri* Dubey and Lindsay, 1999 Parasite from the South American Opossum (*Didelphis albiventris*) from Argentina.

Hamir et al., J Vet Diagn Invest 5:418-422 (1993), Immunohistochemical study to demonstrate *Sarcocystis neurona* in equine protozoal myeloencephalitis.

Granstrom et al., J Vet Diagn Invest 5:88-90 (1993), Equine protozoal myeloencephalitis: antigen analysis of cultured *Sarcocystis neurona* merozoites.

Dubey et al., J Parasitology 77(2) 1991 212-218, *Sarcocystis neurona* N. SP. (Protozoa: Apicomplexa), the Etiologic Agent of Equine Protozoal Myeloencephalitis.

Bentz et al., JAVMA vol. 210 No. 4 Feb. 15, 1997, 517-518, Seroprevalence of antibodies to *Sarcocystis neurona* in horses residing in a county of southeastern Pennsylvania.

Blythe et al., JAVMA vol. 210 No. 4 Feb. 15, 1997, 525-527, Seroprevalence of antibodies to *Sarcocystis neurona* in horses residing in Oregon.

Murrell et al., Vaccines; New Concepts & Developments, Ed. Heinz Kohler & Phillip T. Laverde Proceeding of the 10th International Convention of Immunology, Buffalo, NY Jul. 14-17, 1986, pp. 403-411, , Vaccines against animal parasites.

Dubey et al., Sarcocystosis of Animals and Man, 1989, 1-115, by CRC Press Inc, Boca Raton, FL.

Noble et al., Parasitology The Biology of Animal Parasites 5th Edition, Lea & Febiger Philadelphia 1982, p-85, Phylum Apicomplexa.

Gregory L. Ferraro, DVM, Equis Magazine 262, Aug. 1999, EPM: A New Plan of Attack, 11-13.

John B. Dame, AVMA Conference, New Orleans LA Jul. 1999, EPM: possums, parasites and paresis, 522-525.

Fayer et al., International Journal of Parasitology, 1987 vol. 7(2) 615-620, Comparative Epidemiology of Coccidia: Clues to the Etiology of Equine Protozoal Myeloencephalitis.

Equine Disease Quarterly, Apr. 1998, vol. 6, No. 3—9 pages.

Equine Disease Quarterly, Jul. 1998, vol. 6, No. 4—6 pages.

Dubey et al., Journal Vet Invest 5:467-471 (1993) meningoencephalitis in mink associated with a *Sarcocystis neurona*-like organism.

Dubey et al., Journal Parasitology 82(1) 1996 172-174, A *Sarcocystis neurona*-like Organism Associated with Encephalitis in a Striped Skunk (*Mephitis mephitis*).

Marsh et al., Parasitology Res (1997) 83: 706-711, Experimental infection of nude mice as a model for *Sarcocystis neurona*-associated encephalitis.

Christine Barakat, Equuus Magazine (268) Feb. 2000, pp. 15-16, Neospora Hughesi.

Gajadhar et al., Journal Parasitology 84(4), 1998 759-763, Prevalence of Toxoplasma Gondii in Canadian Market-Age Pigs.

John Lyons, John Lyons' Perfect Horse Mar. 2000, 22-24, Common Questions About EPM.

Saville et al., JAVPM vol. 217 No. 8 Oct. 2000, 1181-1185, Evaluation of risk factors associated with clinical improvement and survival of horses with equine protozoal myeloencephalitis.

Ramey, David W., Equine Athlete, Sep./Oct. 1997, pp. 11-12, EPM: Research and Destroy.

Lindsay et al, Veterinary Parisitology, (Sep. 20, 2000), 92 (2) 157-163, Inoculation of *Sarcocystis neurona* Merozites into the Central Nervous System of Horses.

Dubey et al, Veterinary Parisitology, (Feb. 26, 2001), 95/2-4 (89-131), A Review of *Sarcocystis neurona* and Equine Protozoal Myeloencephalitis.

* cited by examiner

EQUINE PROTOZOAL MYELOENCEPHALITIS VACCINE

This application claims priority from copending provisional application(s) Ser. No. 60/199,435 filed on Apr. 25, 2000 and provisional application Ser. No. 60/278,695 filed on Mar. 26, 2001.

BACKGROUND OF THE INVENTION

Equine protozoal myeloencephalitis (EPM) is a debilitating neurologic disease of equines which can affect the brain, the brain stem, spinal cord or any combination of these three areas of the equine's central nervous system. EPM is caused by the protozoan parasites *Sarcocystis neurona* or *Neospora hughesi*.

A horse of any age, breed or gender may be affected by EPM. The disease has been reported in two-month olds, as well as thirty-year olds. In fact, any horse demonstrating neurologic abnormalities may be infected. Clinical signs of a condition depend upon the location of the organism within the central nervous system. These signs include weakness, malposition of a limb, muscle atrophy, spinal ataxia or the like. A severely EPM-affected horse may go down and be unable to rise. Lameness not traceable to orthopedic disease or any combination of the aforementioned signs may occur in early or less severe infections.

Initially EPM was thought to only be caused by *Sarcocystis neurona*. The opossum (*Didelphis virginiana*) has been identified as the definitive host for this agents. The intermediate host for this organism is still unknown. The horse ingests feed which has been contaminated with opossum fecal material containing *Sarcocystis neurona* sporocysts. These sporocysts then excyst in the intestinal epithelium of the intermediate and incidental hosts. In the case of the intermediate host, the merezoites would encyst in the tissues of the host forming sarcocysts. In the case of the aberrant host, the *Sarcocystis neurona* multiply in the Central Nervous System (spinal cord) and fail to encyst. In horses, the only observed forms of *Sarcocystis neurona* have been the meront or merozoite.

Recently *Neospora hughesi* has been identified as a second organism which will cause the EPM clinical disease. *Neospora hughesi* will not only infect the spinal cord as *Sarcocystis neurona* does, but will also colonize the brain. At this point in time the definitive and intermediate hosts for *Neospora hughesi* remain unknown. It is believed that fecal contamination of horse feed or water with sporulated oocysts is the route of horse infection. The oocysts will release tachyzoites which will infect cells as do the merozoites of *Sarcocystis neurona*.

In both cases the horse is an aberrant dead-end host and infectious forms of the parasite are not passed from horse to horse or from an infected horse to a definitive or true intermediate host.

There is currently no vaccine or approved animal drug product available for the effective treatment of EPM. The currently available treatments are expensive, of limited efficacy and may include adverse side effects such as anemia, abortion, diarrhea, low white blood cell counts or the like. There remains an unfulfilled need for treatment for EPM-afflicted equines, particularly horses, which is effective, convenient to administer and useful for the reduction of resistant strains.

Therefore, it is an object of this invention to provide an immunogenically active component useful for the prevention or amelioration of EPM.

It is another object of this invention to provide a vaccine composition suitable for use in equines against infection and disease caused by the protozoan parasites *Sarcocystis neurona* and/or *Neospora hughesi*.

It is a further object of this invention to provide a method for the prevention or amelioration of EPM disease in equines that need such protection. Other objects and features of the invention will become apparent from the detailed description set forth herein below.

SUMMARY OF THE INVENTION

The present invention provides an immunogenically active component which comprises inactivated *Sarcocystis neurona* cells or inactivated *Neospora hughesi* cells; DNA derived therefrom; or a mixture; or in combination with other vaccine components.

The present invention further provides an immunogenically active component which comprises a member selected from the group consisting of merozoite antibody inducing, inactivated *Sarcocystis neurona* cells; tachyzoite antibody inducing, inactivated *Neospora hughesi* cells; a merozoite or tachyzoite antibody inducing antigen derived or extracted from said cells; DNA derived from said cells capable of inducing a merozoite or tachyzoite antibody immune response; and a mixture thereof.

Further provided is a vaccine composition which comprises an effective immunizing amount of at least one of the above-said immunogenically active components and a pharmacologically acceptable carrier.

Still further provided is a vaccine composition which comprises a) an effective amount of one immunologically active component selected from merozoite antibody inducing, inactivated *Sarcocystis neurona* cells; a merozoite antibody inducing antigen derived or extracted from said cells; DNA derived from said cells capable of inducing a merozoite antibody immune response, and a mixture thereof; b) an effective amount of a second immunologically active component selected from tachyzoite antibody inducing, inactivated *Neospora hughesi* cells; a tachyzoite antibody inducing antigen derived or extracted from said cells; DNA derived from said cells capable of inducing a tachyzoite antibody immune response; and a mixture thereof; and c) a pharmacologically acceptable carrier.

The present invention also provides a method for the prevention or amelioration of infection or disease caused by *Sarcocystis neurona* protozoa in equines that need such protection. The method for the prevention or amelioration of EPM infection or disease in equines comprises administering to said equine an immunogenically active component which comprises a member selected from the group consisting of merozoite antibody inducing, inactivated *Sarcocystis neurona* cells; tachyzoite antibody inducing, inactivated *Neospora hughesi* cells; a merozoite or tachyzoite antibody inducing antigen derived from said cells; DNA derived from said cells capable of inducing a merozoite or tachyzoite antibody immune response; or a mixture thereof; and, optionally, a pharmacologically acceptable carrier.

Also provided is a method for the cell culture propagation of protozoan parasites, including *Sarcocystis* spp. and *Neospora* spp.

DETAILED DESCRIPTION OF THE INVENTION

*Sarcocystis neurona* or *Neospora hughesi* protozoa are the causative agents of equine protozoal myeloencephalitis (EPM) disease, which is a serious, and sometimes fatal, neurological disease in equines, particularly horses. EPM symptoms include hypermetria, decreased proprioception, weakness, cranial nerve deficits, general ataxia or the like. The opossum has been identified as the definitive host for these organisms. However an intermediate host is, as yet, unknown. Equines are the aberrant host and apparently become infected when ingesting feed which has been contaminated with the *Sarcocystis neurona* or *Neospora hughesi* protozoans via opossum fecal contamination. EPM disease when untreated will progress from initial numbness of limbs to final central nervous system destruction, resulting in death. Heretofore, there were no known vaccination or immunization treatments available against EPM.

Surprisingly, it has now been found that an immunogenically active component which comprises inactivated *Sarcocystis neurona* cells or antigens, subunit proteins or plasmid DNA; inactivated *Neospora hughesi* cells or antigens, subunit proteins or plasmid DNA; or mixtures thereof may be administered in the form of a vaccine composition to prevent or ameliorate EPM disease in equines, particularly horses. Antigens derived from *Sarcocystis neurona* or *Neospora hughesi* may be obtained using conventional procedures such as outer membrane extraction. Plasmid DNA derived from *Sarcocystis neurona* or *Neospora hughesi* may be obtained via isolation from sources such as the fluids or tissues of equine mammalians diagnosed to have EPM. Such sources include cerebral spinal fluid or sections of spinal cord or brain. Alternatively, the precursor of the infectious stage in horses (sporocyst or cyst) may be obtained from feces or intestinal scrapings of opossums or other wild life present in endemic locales. *Sarcocystis* Spp. or *Neospora* SPP. cells, thus obtained, may be maintained in the infected equine or in suitable tissue culture media, such as RPMI 1640 medium or in cells known in the art such as African green monkey kidney (Vero) cells or equine dermal (E. Derm) cells. The *Sarcocystis* Spp. or *Neospora* Spp. protozoa may then be separated from the tissue culture of cell media using conventional techniques such as centrifugation, filtration, or the like. A useful starting isolate for the vaccines of the invention include, for example, for *Sarcocystis neurona*, the isolate designated SN3; other such isolates are those known as SN1, SN2, SN4, SN5, SN6, UCD-1, UCD-2 and UCD-3 and are variously available from the University of Kentucky, Dr. J.P Dubey at the USDA, U. of California— Davis, Oregon State University, the University of Missouri and others. A culture of one such *Sarcocystis neurona* isolate designated SNg, originally isolated from the intestinal scrapings of the opossum and confirmed to be a representative *Sarcocystis neurona* by PCR, was deposited on Jan. 25, 2001 in the American Type Culture Collection (ATCC), 10801 University Boulevard, Manassas, Va. 20110-2209, U.S.A., and given ATCC Accession No. PTA-2972. The deposit was made under the conditions mandated by 37 C.F.R § 1.808 and is being maintained pursuant to the Budapest Treaty. A useful starting isolate for the vaccines of the invention include, for example, for *Neospora hughesi*, the isolate designated NEQ1; another such isolate is that known as NE1, which has been described by Antoinette Marsh et al, Journal of Parasitology, 84 (5), 1998, pp 983–991. A culture of one such *Neospora hughesi* isolate has been deposited with the ATCC and given ATCC Accession No. 209622 (NE1) as disclosed in U.S. Pat. No. 6,071,737. Surprisingly, it has now been found that protozoan parasites such as *Sarcocystis* spp. or *Neospora* Spp. may be propagated in increased yield and increased active viability via cell culture propagation by growing suitable cells to a monolayer having a confluency of about 80%–100% in a growth media; decanting the growth media; refeeding the cells with fresh growth media; inoculating the cells with merozoites or tachyzoites; after 4–12 days, decanting the growth media; and refeeding the inoculated cells a second time with growth media. Cells suitable for use in the method of the invention include cells such as E. Derm cells, Vero cells, Maiden Darby Bovine Kidney (MDBK) cells, Canine Monocyte (DH82) cells, Mouse Monocyte (P388) cells, Fetal Rhesus Monkey Kidney cells, Feline Kidney (FKCU) cells, Maiden Darby Canine Kidney (MDCK) cells, Baby Hamster Kidney (BHK21) cells, or the like, preferably E. Derm or Vero cells, more preferably E. Derm cells.

In actual practice, the cells are grown to a monolayer having at least 80%, preferably 90%–100%, confluency in a growth media such as MEM with 0.05% lacalbumin hydrosylate (LAH) or Optimem (LTI, Gaithersburg, Md.) supplemented with 10% fetal bovine serum, iron fortified fetal calf serum or donor serum. When the cell monolayer has been formed, the culture is decanted to remove the original growth media, the cells are refed with a growth media such as RPMI 1640 with no antibiotics and 25 μM hepes buffer supplemented with 1% sodium pyruvate/2-mercaptoethanol solution having a pH of 6.8–7.8, preferably 7.2–7.4, and up to 10% fetal bovine serum. The refed cells are then inoculated with merozoites or tachyzoites, held for 4 to 12 days and decanted to remove the growth media. The culture is then refed a second time with growth media as described above and monitored for disease progression. When a level of cytopathology of >60% is obtained, the culture may be harvested.

The thus-obtained whole cell isolates of *Sarcocystis* Spp. or *Neospora* Spp. protozoa may be inactivated by conventional inactivating means, for example chemical inactivation using chemical inactivating agents such as binary ethyleneimine, beta-propiolactone, formalin, merthiolate, gluteraldehyde, sodium dodecyl sulfate, or the like or a mixture thereof, preferably formalin. Said whole cell isolates may also be inactivated by heat or psoralen in the presence of ultraviolet light.

As used herein the term "immunogenically active" designates the ability to stimulate an immune response, i.e., to stimulate the production of antibodies, particularly humoral antibodies, or to stimulate a cell-mediated response. For example, the ability to stimulate the production of circulating or secretory antibodies or the production of a cell-mediated response in local mucosal regions, i.e., intestinal mucosa, peripheral blood, cerebral spinal fluid or the like.

The immunogenically active component of the invention may be incorporated into liposomes using known technology such as that described in Nature, 1974, 252, 252–254 or Journal of Immunology, 1978, 120, 1109–13. Further, the immunogenically active component of the invention may be conjugated to suitable biological compounds such as polysaccharides, peptides, proteins, or the like, or a combination thereof.

Advantageously, the immunogenically active component of the invention may be formulated as a vaccine composition in dosage unit form to facilitate administration and insure uniformity of dosage. The vaccine composition of the invention comprises an effective immunizing amount of the immunogenically active component described hereinabove, a pharmacologically acceptable carrier and optionally an immunogenically stimulating adjuvant. The effective immunizing amount of the immunogenically active component may vary and may be any amount sufficient to evoke an immune response. Amounts wherein the dosage unit comprises at least about $1 \times 10^4$ inactivated *Sarcocystis* Spp. cells or *Neospora* Spp. cells or a mixture thereof, preferably at least about $1 \times 10^6$ cells, are suitable.

As used in the specification and claims, the term "immunogenically stimulating adjuvant" designates a compound which is capable of potentiating or stimulating the immune response in a subject animal when administered in combination with the immunogenically active component of the invention. Examples of an immunogenically stimulating adjuvant suitable for use in the vaccine composition of the invention include: surfactants such as hexadecylamine, octadecylamine, lysolecithin, dimethyl dioctadicyl ammonium bromide, N,N-dioctadecyl-N'-N-bis(2-hydroxyethyl-propane diamine), methoxyhexadecylglycerol, polyoxyethylene-polyoxypropylene block coplymer PLURONIC polyols, saponin, Quil® A, or the like; polyanions such as pyran, dextran sulfate, polynucleotide complex of polyinosinicpolycytidylic acid, polyacrylic acid, carboxypolymethylenes and carboxyvinyl polymers such as CARBOPOL®, aluminum hydroxide, aluminum phosphate, or the like; peptides such as muramyl dipeptide, dimethyl glycine, tuftsin or the like; oil emulsions; immunomodulators such as interleukin-1, interleukin-2, interleukin-12, GM-CSF or the like; or a combination thereof. A preferred immunogenically stimulating adjuvant suitable for use in the vaccine composition of the invention is a mixture of squalane and a polyoxyethylene-polyoxypropylene block copolymer (e.g., Pluronic® L121, BASF, Parsippany, N.J.) capable of forming small liposomes. The immunogenically stimulating adjuvant may be present in the vaccine composition of the invention in wt/wt amounts of about 1% to 50%, preferably about 5% to 20%.

Pharmacologically acceptable carriers suitable for use in the vaccine composition of the invention may be any conventional liquid carrier suitable for veterinary pharmaceutical compositions, preferably a balanced salt solution suitable for use in tissue culture media.

In addition to the immunogenically active component as active ingredient, it is contemplated the vaccine composition of the invention may also contain other active components such as an antipathogenic component directed against rabies virus, Eastern equine encephalitis virus, Western equine encephalitis virus, Venezuelan equine encephalitis virus, equine herpes virus such as EHV-1 or EHV-4, *Ehrlichia risticii, Streptococcus equi*, tetanus toxoid, or the like or a combination thereof.

The inventive vaccine composition may be administered parenterally, for example, intramuscularly, subcutaneously, intraperitoneally, intradermally or the like, preferably intramuscularly; or said composition may be administered orally or intranasally.

The vaccine composition of the invention is useful for the prevention or amelioration of EPM infections in equine that need such protection. In actual practice, the vaccine composition of the invention is administered parenterally, orally, or intranasally, preferable parenterally, more preferably intramuscularly, in effective amounts according to a schedule determined by the time of potential exposure to infective *Sarcocystis* Spp. or *Neospora* Spp. sporocysts. In this way, the treated animal may have time to build immunity prior to natural exposure. For example, a typical treatment schedule may include parenteral administration, preferably intramuscular injection, at least 5–8 weeks prior to potential exposure. At least two administrations are preferred, for example one at about 8 weeks and a second at about 3 weeks prior to potential exposure of the treated animal.

For a more clear understanding of the invention, the following examples are set forth below. These examples are merely illustrative and are not understood to limit the scope or underlying principles of the invention in any way. Indeed, various modifications of the invention, in addition to those shown and described herein, will become apparent to those skilled in the art from the following examples and the foregoing description. Such modifications are also intended to fall with the scope of the appended claims.

Unless otherwise noted, all parts are parts by weight.

EXAMPLE 1

A—Vaccine Preparation

An equine spinal cord isolate of *Sarcocystis neurona* is obtained from a horse which has been diagnosed to have EPM. The isolate is cultivated in multiple cultures of E. Derm cells in RPMI tissue culture medium at 37° C. These merozoite harvests are counted at the time of harvest and then inactivated by means of addition of a 10% formalin solution to a final concentration of 0.05%. This is allowed to inactivate at 37° C. for a period of no less than 48 hours.

To remove unnecessary serum proteins associated with tissue culture the harvests are pooled and diafiltrated/concentrated against 0.01M phosphate buffered saline to a level of $3.14\times10^7$ merozoites per mL.

The vaccines are formulated by suspending the appropriate volume of inactivated cells in an adjuvant containing 1–20% by volume of a metabolizable oil adjuvant per 1 mL dose, e.g., 5% of the stock adjuvant described herinbelow.

B—Formulation of a Preferred Stock Adjuvant

A preferred adjuvant for use in the present invention was prepared according to the following formulation:

| | |
|---|---|
| Polyoxyethylene-polyoxypropylene block copolymer (e.g., Pluronic ® L121, BASF, Parsippany, NJ) | 20 ml |
| Squalane (e.g, Kodak, Rochester, NY) | 40 ml |
| Polyoxyethylenesorbitan monooleate (e.g., Tween ® 80, Sigma Chemical, St. Louis, MO) | 3.2 ml |
| buffered salt solution (e.g., D-V PAS Solution, Ca, Mg free) | 936.8 ml |

The ingredients are mixed and homogenized until a stable mass or emulsion is formed. Prior to homogenization, the ingredients or mixture can be autoclaved. The emulsion may be further sterilized by filtration. Formalin may be added up to a final concentration of 0.2%. Thimerosal may be added to a final dilution of 1:10,000.

EXAMPLE 2

Antibody Response to Intramuscular Injection of Vaccine

In this evaluation, horses that are found to be naive to *Sarcocystis neurona* merozoite antigen by means of Indirect Fluorescent Antibody (IFA) testing are employed. Horses are randomly divided into four groups: one group of nine horses are administered vaccine at the level of $1\times10^5$ merozoites per dose; a second group of twenty-one horses are administered vaccine blended at $1\times10^6$ merozoites per dose; a third group of ten horses are administered vaccine at $1\times10^7$ merozoites per dose; and a fourth of group of ten horses are maintained as non-vaccinated environmental controls. Treated horses are given a first dose of vaccine according to the group to which they are assigned. At twenty-one days following administration of the first dose, a second dose of the same vaccine is administered. All horses are bled for serum at the time of administration of the first and second dose and at weekly intervals through 28 days post second dose administration.

In this evaluation, the vaccine compositions contain formalin-inactivated, E. Derm cell line-grown *Sarcocystis neurona* merozoites with an adjuvant system. The method of serologic measurement of antibodies is conducted by IFA. The IFA is run using Vero cell line-grown *Sarcocystis neurona* merozoites to eliminate anti-E. Derm antibody titers.

The serological data is shown in Table I below, wherein: 0 DPV 1 designates day zero, pre vaccination; 0 DPV 2 designates day zero, post vaccination; 7 DPV 2 designates day 7, post vaccination; and 14 DPV 2 designates day 14, post vaccination.

As can be seen from the data on Table I, treated horses from all groups showed significant increases in antibodies to *Sarcocystis neurona* merozoites while the control horses maintained a low to non-existent antibody level. The level of response in the horses that received vaccine was dependent upon the level of antigen in the vaccine that they received.

TABLE I

EPM (*Sarcocystis neurona*) Dose Titration IFA Serology

| No. | Vaccine | Antigen Load | 0 DPV 1 | 0 DPV 2 | 7 DPV 2 | 14 DPV 2 |
|---|---|---|---|---|---|---|
| 1 | 1 | 1 × 10^5 mer. | <1:10 | 1:80 | 1:640 | 1:800 |
| 2 | 1 | 1 × 10^5 mer. | <1:10 | 1:480 | 1:480 | 1:3200 |
| 3 | 1 | 1 × 10^5 mer. | <1:10 | 1:40 | 1:320 | 1:800 |
| 4 | 1 | 1 × 10^5 mer. | <1:10 | 1:160 | 1:320 | 1:3200 |
| 5 | 1 | 1 × 10^5 mer. | <1:10 | 1:320 | 1:480 | 1:3200 |
| 6 | 1 | 1 × 10^5 mer. | <1:10 | 1:320 | 1:160 | 1:1600 |
| 7 | 1 | 1 × 10^5 mer. | <1:10 | 1:40 | 1:80 | 1:400 |
| 9 | 1 | 1 × 10^5 mer. | <1:10 | 1:320 | 1:160 | 1:800 |
| 10 | 1 | 1 × 10^5 mer. | <1:10 | 1:480 | 1:640 | 1:4800 |
| GMT | | | <1:10 | 1:211 | 1:300 | 1:1550 |
| 11 | 2 | 1 × 10^6 mer. | <1:10 | 1:640 | 1:960 | 1:4800 |
| 12 | 2 | 1 × 10^6 mer. | <1:10 | 1:960 | 1:1920 | 1:4800 |
| 13 | 2 | 1 × 10^6 mer. | <1:10 | 1:160 | 1:240 | 1:800 |
| 14 | 2 | 1 × 10^6 mer. | <1:10 | 1:640 | 1:1280 | 1:4800 |
| 15 | 2 | 1 × 10^6 mer. | <1:10 | 1:1280 | 1:2560 | 1:12000 |
| 16 | 2 | 1 × 10^6 mer. | <1:10 | 1:320 | 1:1280 | 1:4800 |
| 17 | 2 | 1 × 10^6 mer. | <1:10 | 1:320 | 1:640 | 1:3200 |
| 18 | 2 | 1 × 10^6 mer. | <1:10 | 1:1280 | 1:960 | 1:3200 |
| 19 | 2 | 1 × 10^6 mer. | <1:10 | 1:160 | 1:960 | 1:4800 |
| 20 | 2 | 1 × 10^6 mer. | <1:10 | 1:320 | 1:640 | 1:800 |
| 21 | 2 | 1 × 10^6 mer. | <1:10 | 1:320 | 1:640 | 1:4800 |
| 22 | 2 | 1 × 10^6 mer. | <1:10 | 1:960 | 1:1920 | 1:4800 |
| 23 | 2 | 1 × 10^6 mer. | <1:10 | 1:640 | 1:1280 | 1:4800 |
| 24 | 2 | 1 × 10^6 mer. | <1:10 | 1:1280 | 1:2560 | 1:3200 |
| 25 | 2 | 1 × 10^6 mer. | <1:10 | 1:640 | 1:1280 | 1:4800 |
| 26 | 2 | 1 × 10^6 mer. | <1:10 | 1:1280 | 1:960 | 1:3200 |
| 27 | 2 | 1 × 10^6 mer. | <1:10 | 1:1280 | 1:1280 | 1:3200 |
| 28 | 2 | 1 × 10^6 mer. | <1:10 | 1:1280 | 1:1280 | 1:4800 |
| 29 | 2 | 1 × 10^6 mer. | <1:10 | 1:2560 | 1:960 | 1:4800 |
| 30 | 2 | 1 × 10^6 mer. | <1:10 | 1:2560 | 1:2560 | 1:3200 |
| 31 | 2 | 1 × 10^6 mer. | <1:10 | 1:1280 | 1:1280 | 1:3200 |
| GMT | | | <1:10 | 1:734 | 1:1147 | 1:3704 |
| 32 | 3 | 1 × 10^7 mer. | <1:10 | 1:1280 | 1:1920 | 1:3200 |
| 33 | 3 | 1 × 10^7 mer. | <1:10 | 1:640 | 1:1280 | 1:4800 |
| 34 | 3 | 1 × 10^7 mer. | <1:10 | 1:640 | 1:1280 | 1:1600 |
| 35 | 3 | 1 × 10^7 mer. | <1:10 | 1:2560 | 1:2560 | 1:4800 |
| 36 | 3 | 1 × 10^7 mer. | <1:10 | 1:2560 | 1:5120 | 1:4800 |
| 37 | 3 | 1 × 10^7 mer. | <1:10 | 1:2560 | 1:5120 | 1:4800 |
| 38 | 3 | 1 × 10^7 mer. | <1:10 | 1:1280 | 1:1280 | 1:12800 |
| 39 | 3 | 1 × 10^7 mer. | <1:10 | 1:2560 | 1:7680 | 1:19200 |
| 40 | 3 | 1 × 10^7 mer. | <1:10 | 1:1920 | 1:2560 | 1:19200 |
| 41 | 3 | 1 × 10^7 mer. | <1:10 | 1:1280 | NS | 1:12800 |
| GMT | | | <1:10 | 1:1429 | 1:2296 | 1:6630 |
| 42 | 4 | Control | <1:10 | <1:10 | <1:10 | <1:10 |
| 43 | 4 | Control | <1:10 | <1:10 | <1:10 | <1:10 |
| 44 | 4 | Control | <1:10 | <1:10 | <1:10 | <1:10 |
| 45 | 4 | Control | <1:10 | <1:10 | <1:10 | <1:10 |
| 46 | 4 | Control | <1:10 | <1:10 | <1:10 | <1:10 |
| 47 | 4 | Control | <1:10 | <1:10 | <1:10 | <1:10 |
| 48 | 4 | Control | <1:10 | <1:10 | <1:10 | <1:10 |
| 49 | 4 | Control | <1:10 | <1:10 | <1:10 | <1:10 |
| 50 | 4 | Control | <1:10 | <1:10 | <1:10 | <1:10 |
| 51 | 4 | Control | <1:10 | <1:10 | <1:10 | <1:10 |
| GMT | | | <1:10 | <1:10 | <1:10 | <1:10 |

| Sample | Type | Material | IFA Titer |
|---|---|---|---|
| MSU1 | Positive | Control Sera | 1:800 |
| MSU2 | Positive | Control Sera | 1:800 |
| Blakely | Positive | Control Sera | 1:400 |
| Sport | Positive | Control Sera | 1:160 |

EXAMPLE 3

Plaque Reduction Effect as Determined by Serum of Vaccinated Horses

In this evaluation, an assay is performed to determine if the *Sarcocystis neurona* antibody found by IFA in the serum of EPM vaccinated horses would have a neutralizing effect on *Sarcocystis neurona* merozoites at varying levels of the organism.

Horse serum samples are collected at 14 days post second vaccination from the Example 2 study group 3, which received vaccine containing $1 \times 10^7$ merozoites per dose; and the samples are pooled. Duplicate sets of this serum are diluted 1:2 to a 1.0 mL volume and are mixed with 1.0 mL volumes of varying levels of viable *Sarcocystis neurona* merozoites, resulting in a final serum dilution of 1:4. The organism (merozoite) levels used 1:10 are $2.5 \times 10^5$, 1:100 are $2.5 \times 10^4$, and 1:1000 are $2.5 \times 10^3$ merozoites per mL. Duplicate sets of serum/organism tubes are set up using a serum pool from the group 4 non-vaccinated horses to stand as a negative control group for comparison. The 2.0 mL organism/serum mixtures are incubated for 1 hour at 37° C. and then added to 25 cm² of E. Derm cells with the appropriate media to support *Sarcocystis neurona*. At 14 days post inoculation all flasks are fixed using a 10% formalin/crystal violet stain and are counted for the number of plaques present in each flask.

There was a marked reduction in the number of plaques observed in the flasks which had received the serum from the group 3 vaccinate horses which had been incubated with organism at all organism dilutions when compared to similar flasks which had the non-vaccinated control serum. This data is shown in Table II below.

As can be seen from the data in Table II, the degree of plaque reduction in every case of the vaccinated horse serum pools exceeded 70%.

TABLE II

*Sarcocystis neurona* Plaque Reduction Serology

| Organism Dilution | Sample | Serum Dilution | Observed | Average No. of Plaques | Percent Reduction[2] |
|---|---|---|---|---|---|
| 1:10 | Vaccine 3 | 1:4 | 87 | 97.0 | 89.22 |
| 1:10 | Vaccine 3 | 1:4 | 107 | | |
| 1:100 | Vaccine 3 | 1:4 | 16 | 14.0 | 73.33 |
| 1:100 | Vaccine 3 | 1:4 | 12 | | |
| 1:1000 | Vaccine 3 | 1:4 | 2 | 1.5 | 85.00 |
| 1:1000 | Vaccine 3 | 1:4 | 1 | | |
| 1:10 | Controls | 1:4 | TNTC[1] | TNTC | NA |
| 1:10 | Controls | 1:4 | TNTC | | |
| 1:100 | Controls | 1:4 | 55 | 52.5 | NA |
| 1:100 | Controls | 1:4 | 50 | | |
| 1:1000 | Controls | 1:4 | 12 | 10.0 | NA |
| 1:1000 | Controls | 1:4 | 8 | | |

[1]TNTC estimated to be 900–1000 plaques (900 used for calculations).
[2]Percent Reduction as compared to the number of plaques in the corresponding control serum dilution plaque count.

EXAMPLE 4

Vaccine Preparation

*Neospora hughesi* is obtained from the brain or spinal column of a horse that has been diagnosed to have EPM. The isolate is cultivated in multiple cultures of E. Derm or Vero cells in RPMI tissue culture medium at 37° C. The tachyzoites harvested are counted at the time of harvest and then inactivated by means of addition of a 10% formalin solution to a final concentration of 0.05%. This is allowed to inactivate at 37° C. for a period of no less than 48 hours.

To possibly remove unnecessary serum proteins associated with tissue culture the harvests are pooled and may be diafiltrated/concentrated against 0.01M phosphate buffered saline to a suitable level of tachyzoites per mL for final vaccine formulation.

The vaccine is formulated with antigen as in Example 1.

EXAMPLE 5

Cell Culture Propagation of *Sarcocystis* spp. and *Neospora* spp.

Equine dermal (E. derm) cells that have been grown to achieve a monolayer of 90–100% confluency are decanted to remove the original cell growth media (OptiMEM supplemented with 10% fetal bovine serum). The E. derm cells are then refed with RPMI 1640 media supplemented with 1% sodium pyruvate/2-mercaptoethanol[1] solution having a pH of 7.2–7.4 and 10% fetal bovine serum and inoculated with viable merozoites or tachyzoites. After 4–12 days, the resultant culture is decanted to remove the growth media and then refed a second time with RPMI 1640 media supplemented with 1% sodium pyruvate/2-mercaptoethanol solution[1] having a pH of 7.2–7.4 and 2%–10% bovine fetal serum. The resultant culture is then monitored for disease progression and when a level of greater than 60% cytopathology is obtained the culture is harvested.

[1]The sodium pyruvate/2-mercaptoethanol solution consists of 0.175 mL 2-mercaptoethanol and 0.600 g sodium pyruvate in 500 mL of RPMI 1640 media (pH 7.2–7.4) which has been sterile filtered.

What is claimed is:

1. An isolated and purified *Sarcocystis neurona* strain designated SNg, having ATCC Accession No. PTA-2972 or a subculture thereof.

2. An immunogenically active component useful for preventing or ameliorating equine protozoal myoencephalitis disease which comprises merozoite antibody-inducing whole cells of a *Sarcocystis neurona* isolate designated SNg, having ATCC Accession No. PTA-2972 or a subculture thereof.

3. The immunogenically active component according to claim 2 wherein the whole cells of the *Sarcocystis neurona* isolate or the subculture thereof are inactivated.

4. The immunogenically active component according to claim 3 wherein the whole cells of the *Sarcocystis neurona* isolate or the subculture thereof are present in sufficient quantity to provide at least $1 \times 10^4$ inactivated cells per dosage unit form.

5. A method for the prevention or amelioration of equine protozoal myoencephalitis disease in an equine which comprises administering to said equine the immunogenically active component of claim 3.

6. A vaccine composition for the prevention or amelioration of equine protozoal myoencephalitis disease in an equine which comprises a therapeutically effective amount of the immunogenically active component of claim 3, a pharmacologically acceptable carrier and optionally an immunogenically stimulating adjuvant.

7. The vaccine composition according to claim 6 wherein said active component is present in sufficient quantity to provide at least $1\times10^4$ inactivated cells per dosage unit form.

8. The vaccine composition according to claim 6 wherein said active component is present in sufficient quantity to provide at least $1\times10^6$ inactivated cells per dosage unit form.

9. The vaccine composition according to claim 6 wherein said active component is present in an amount sufficient to produce a merozoite inducing serum neutralizing antibody response which has a neutralizing effect on *Sarcocystis neurona* merozoites.

10. The vaccine composition according to claim 6 wherein the immunogenically stimulating adjuvant is present at about 1% to 50% by weight.

11. The vaccine composition according to claim 10 wherein said adjuvant is present at about 5% to 20% by weight.

12. The vaccine composition according to claim 10 wherein said adjuvant is a metabolizable oil.

13. The vaccine composition according to claim 12 wherein the pharmacologically acceptable carrier is a balanced salt solution.

14. A method for the prevention or amelioration of equine protozoal myoencephalitis disease in an equine which comprises administering to said equine a therapeutically effective amount of the vaccine composition of claim 6.

15. The method according to claim 14 wherein said vaccine is administered parenterally.

16. The method according to claim 14 wherein said vaccine is administered intramuscularly.

* * * * *